(12) United States Patent
Fant (10) Patent No.: US 9,260,641 B2
(45) Date of Patent: Feb. 16, 2016

(54) DRYABLE ADHESIVE COATING

(75) Inventor: Camilla Fant, Kullavik (SE)

(73) Assignee: Biopolymer Products of Sweden AB, Molnlycke (SE)

(*) Notice: Subject to any disclaimer, the term of this patent is extended or adjusted under 35 U.S.C. 154(b) by 66 days.

(21) Appl. No.: 14/116,816

(22) PCT Filed: May 8, 2012

(86) PCT No.: PCT/EP2012/058422
§ 371 (c)(1),
(2), (4) Date: Mar. 13, 2014

(87) PCT Pub. No.: WO2012/152781
PCT Pub. Date: Nov. 15, 2012

(65) Prior Publication Data
US 2014/0186410 A1 Jul. 3, 2014

Related U.S. Application Data

(60) Provisional application No. 61/483,807, filed on May 9, 2011.

(30) Foreign Application Priority Data

May 9, 2011 (SE) .................................. 1150407-3

(51) Int. Cl.
| | | |
|---|---|---|
| A61L 24/00 | (2006.01) | |
| C09J 189/00 | (2006.01) | |
| C07K 14/435 | (2006.01) | |
| A61L 24/10 | (2006.01) | |
| A61L 27/00 | (2006.01) | |
| A61L 31/00 | (2006.01) | |

(52) U.S. Cl.
CPC ........... *C09J 189/00* (2013.01); *A61L 24/0015* (2013.01); *A61L 24/0073* (2013.01); *A61L 24/108* (2013.01); *A61L 27/00* (2013.01); *A61L 31/00* (2013.01); *C07K 14/43504* (2013.01); *C09J 189/005* (2013.01); *A61L 2300/404* (2013.01); *Y10T 428/2848* (2015.01); *Y10T 428/2865* (2015.01)

(58) Field of Classification Search
CPC ..................... A61L 2300/404; A61L 24/0015; A61L 24/0073; A61L 24/108; A61L 27/00; A61L 31/00; C07K 14/43504; C09J 189/00; C09J 189/005
See application file for complete search history.

(56) References Cited

U.S. PATENT DOCUMENTS

| | | |
|---|---|---|
| 5,015,677 A | 5/1991 | Benedict et al. |
| 6,506,577 B1 | 1/2003 | Deming et al. |
| 2005/0201974 A1* | 9/2005 | Schestopol et al. ........ 424/78.27 |

FOREIGN PATENT DOCUMENTS

| | | |
|---|---|---|
| WO | 03/051418 A1 | 6/2003 |
| WO | 03/080137 | 10/2003 |
| WO | 2004/005421 A1 | 1/2004 |
| WO | 2006/038866 A1 | 4/2006 |
| WO | 2012/007199 A1 | 1/2012 |

OTHER PUBLICATIONS

Lin et al., PNAS, 2007, 104(10), 3782-3786.*
International Preliminary Report on Patentability for corresponding International Application No. PCT/EP2012/058422 dated Nov. 12, 2013.
International Search Report and Written Opinion for corresponding International Application No. PCT/EP2012/058422 dated Jul. 24, 2012.
Wang et al., "Co-polypeptides of 3,4-dihydroxyphenylalanine and L-lysine to mimic marine adhesive protein", Biomaterials, Elsevier Science Publishers BV., vol. 28, No. 23, May 14, 2007, pp. 3456-3468.
Guvendiren et al., "Self-Assembly and Adhesion of DOPA-Modified Methacrylic Triblock Hydrogels", Biomacromolecules, vol. 9, No. 1, Jan. 1, 2008, pp. 122-128.
Van Der Leeden, "Are Conformational Changes, Induced by Osmotic Pressure Variations, the Underlying Mechanism of Controlling the Adhesive Activity of Mussel Adhesive Proteins?", Langmuir, vol. 21, No. 24, Nov. 1, 2005, pp. 11373-11379.
Ninan et al., "Adhesive strength and curing rate of marine mussel protein extracts on porcine small intestinal submucosa", Acta Biomaterialia, vol. 3, No. 5, Aug. 10, 2007, pp. 687-694.
Krivosheeva et al., "Adsorption of Mefp-1: Influence of pH on adsorption kinetics and adsorbed amount", Journal of Colloid and Interface Science, vol. 379, No. 1, Aug. 1, 2012, pp. 107-113.

* cited by examiner

*Primary Examiner* — Abigail Fisher
(74) *Attorney, Agent, or Firm* — Renner, Otto, Boisselle & Sklar, LLP (57) ABSTRACT

A dried adhesive coating is manufactured by steps of: a) providing a composition comprising a solution of a polymer, wherein at least 1 wt % of said polymer based on the molecular weight Mw are catechol groups, and wherein the concentration of said polymer in said composition is from 0.1 to 250 mg/ml, b) adjusting the pH of the composition to a value from about 6 to about 7, either (i) before applying the composition to the surface to be coated or (ii) after applying the composition to the surface to be coated, c) applying the composition to the surface to be coated to obtain an adhesive coating on at least a part of the surface, and d) drying the coating.

14 Claims, 8 Drawing Sheets

DRYABLE ADHESIVE COATING

This application is a national phase of International Application No. PCT/EP2012/058422, filed May 8, 2012, and published in the English language which claims priority to SE 1150407-3, filed May 9, 2011, and U.S. 61/483,807, filed May 9, 2011, the disclosures of which are incorporated herein by reference in their entirety.

TECHNICAL FIELD

The present invention relates generally to a method for applying an adhesive coating to the surface of an object and further for attaching surfaces to each other.

BACKGROUND

In prior art it is well known that when the pH of a protein comprising DOPA residues is raised above about 5, auto oxidation of DOPA to dopaquinone is achieved. It is well known that this auto oxidation is faster with a higher pH.

In adhesive compositions intended for biological tissue it is not suitable to have very high or very low pH. From a perspective of sensitive tissues a pH value of about 5.5 to 7.5 is often suitable. It was always anticipated that such a low pH give too slow curing of the adhesive. Previous strategies to increase the speed of the adhesion have been to raise pH, as disclosed in WO 2003/051418, to lower the pH and use a concentrated solution as disclosed in WO 2004/005421, or add periodate ions as disclosed in WO 2003/080137.

WO 2003/051418 discloses method for attaching two surfaces or for coating a surface comprising the steps of a) providing a bioadhesive composition consisting of an aqueous solution of a bioadhesive polyphenolic protein derived from a byssus-forming mussel, which protein comprises 30-300 amino acids and consists essentially of tandemly linked peptide repeats comprising 3-15 amino acid residues, wherein at least 3% and preferably 6-30% of the amino acid residues of said protein are DOPA, wherein the concentration of said protein in said bioadhesive composition is within the range of 10-50 mg/ml; b) providing a strongly alkaline solution with a pH of 10 or more; c) (i) mixing said composition and said strongly alkaline solution and applying the mixture to at least one of two surfaces to be attached to each other or (ii) applying said composition and said strongly alkaline solution sequentially, without any specific order, to at least one of two surfaces to be attached to each other, thereby mixing the bioadhesive composition and the strongly alkaline solution; d) optionally joining said surfaces to each other; and e) leaving said surfaces for sufficiently long time for curing to occur. There is also disclosed a corresponding kit.

WO 2003/051418 further discloses mostly when using the polyphenolic proteins as adhesives the pH has had to be raised to neutral or slightly basic (commonly to from 5.5 to 7.5) in order to facilitate oxidation and curing of the protein. However it is added that curing is slow and results in poor adhesive strength. It is also taught that addition of oxidizers, fillers cross-linking agents often is necessary. The selected pH is from a perspective of adhesives to be used for tissues.

WO 2004/005421 discloses use of a composition as a sole component for attaching two surfaces to each other or for coating a surface, said composition consisting of an acidic aqueous solution of a bioadhesive polyphenolic protein derived from a byssus-forming mussel, which protein comprises 30-300 amino acids and that consists essentially of tandemly linked peptide repeats comprising 3-15 amino acid residues, wherein at least 3% and preferably 6-30% of the amino acid residues of said protein are DOPA, where the pH of said acidic solution is 4 or less, and wherein the concentration said protein is 10-250 mg/ml.

WO 2003/080137 discloses a method for attaching two surfaces or for coating a surface comprising the steps of a) providing a bioadhesive composition consisting of an aqueous solution of a bioadhesive polyphenolic protein, which protein comprises 30-300 amino acids and consists essentially of tandemly linked peptide repeats comprising 3-15 amino acid residues, wherein at least 3% and preferably 6-30% of the amino acid residues of said protein are DOPA; b) providing a preparation comprising periodate ions; c) mixing said bioadhesive composition and preparation comprising periodate ions so that the periodate ions constitutes at least 1.80 mmol/g of the final composition; d) (i) applying the mixture to at least one of two surfaces to be attached to each other or (ii) applying said composition and said preparation comprising periodate ions without any specific order, to at least one of two surfaces to be attached to each other, thereby mixing the bioadhesive composition and preparation comprising periodate ions; e) optionally joining said surfaces to each other; and f) leaving said surfaces for sufficiently long time for curing to occur.

Although the strategies used in the prior art give cured compositions there is room for improvement regarding the adhesive. For instance the strength of the adhesive may be improved.

Another problem in the prior art is how to provide an improved adhesive which can be dried, stored and used after a period of storage.

Yet another problem is how to provide a tissue friendly adhesive.

SUMMARY

It is an object of the present invention to obviate at least some of the disadvantages in the prior art and provide an improved method for applying an adhesive coating to the surface of an object.

Previously technology involving use of proteins with DOPA such as mussel adhesive proteins and MEFP have either involved adjustment of the pH or addition of a curing additive, which promotes the curing.

The inventors have unexpectedly discovered that the curing should not be too fast to obtain maximum adhesion. The adhesive should cure slow and preferably for an extended time. Thus the inventors have unexpectedly discovered a pH optimum as low as pH 6-7 for the strength of the adhesive. This pH optimum is without any additives which promote the curing of the polymer. Further it was discovered that the new adhesive can be dried after application to a surface and stored for subsequent use. The adhesive is further tissue friendly. The coating can be dried and subsequently re-activated by wetting and then utilized for adhesive bonding. For a coating to be dried and stored it is also suitable that the curing is not too fast.

In a first aspect there is provided a method for applying an adhesive coating to the surface of an object, said method comprising the steps of: a) providing a composition comprising a solution of a polymer, wherein at least 1 wt % of said polymer based on the molecular weight Mw are catechol groups, and wherein the concentration of said polymer in said composition is from 0.1 to 250 mg/ml, b) adjusting the pH of the composition to a value from about 6 to about 7, either (i) before applying the composition to the surface to be coated or (ii) after applying the composition to the surface to be coated c) applying the composition at least partially to the surface to be coated to obtain an adhesive coating on at least a part of the surface, and d) drying the adhesive coating.

In a second aspect there is provided an object comprising a dried coating, wherein said coating comprises at least one polymer, wherein at least 1 wt % of the polymer based on the molecular weight Mw are catechol groups.

In a third aspect there is provided a kit for applying an adhesive coating to the surface of an object, said kit comprising: a) a composition comprising a solution of a polymer, wherein at least 1 wt % of the polymer based on the molecular weight Mw are chatechol groups, and wherein the concentration of said polymer in said composition is from 0.1 to 250 mg/ml b) an instruction to adjust the pH of the composition to a value from about 6 to about 7, either (i) before applying the composition to the surface to be coated or (ii) after applying the composition to the surface to be coated and an instruction to apply the composition at least partially to the surface to be coated to obtain an adhesive coating on at least a part of the surface, and c) an instructions to dry the adhesive coating.

Further aspects and embodiments are defined in the appended claims as well as in the detailed description.

One advantage of an embodiment is that the adhesive is tissue friendly.

Another advantage is that the strength of the adhesive is excellent, the adhesion strength of objects which are bonded together by the adhesive coating is improved.

Another advantage is that the adhesive can be dried after application to a surface, stored and used after a period of storage.

A further advantage is that no additional additives to promote the curing are necessary except the pH adjustment.

BRIEF DESCRIPTION OF THE DRAWINGS

The invention is now described, by way of example, with reference to the accompanying drawings, in which.

DETAILED DESCRIPTION

Before the invention is disclosed and described in detail, it is to be understood that this invention is not limited to particular compounds, configurations, method steps, substrates, and materials disclosed herein as such compounds, configurations, method steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

If nothing else is defined, any terms and scientific terminology used herein are intended to have the meanings commonly understood by those of skill in the art to which this invention pertains.

The term "about" as used in connection with a numerical value throughout the description and the claims denotes an interval of accuracy, familiar and acceptable to a person skilled in the art. Said interval is ±10%.

"Adhesive coating" is used herein to denote a coating with the ability to adhere to other surfaces.

"Catechol group" is used herein to denote a chemical group equivalent to 1,2-dihydroxybenzene.

"DOPA-derivative" is used herein to denote a chemical compound based on DOPA. The DOPA-derivative is derived from DOPA by any chemical or physical process. A DOPA-derivative is DOPA with a covalently bound chemical group thereon.

"Drying" is used herein to denote the process when a solvent evaporates from the composition, in particular after the composition has been applied on the surface. The solvent is typically water. The coating is dried when the amount of solvent (water) remaining in the dried coating is in equilibrium with the surrounding so that no more solvent evaporates.

"Film" is used herein to denote a thin layer of material.

"Osmolarity" is used herein to denote solute concentration, defined as the number of osmoles of solute per liter of composition (osmole/L or Osm/L). Osmolarity measures the number of osmoles of solute particles per unit volume of solution.

"Osmole" is used herein to denote the number of moles of a compound that contribute to a solutions or a compositions osmotic pressure.

There is provided a method for applying an adhesive coating to the surface of an object, said method comprising the steps of: a) providing a composition comprising a solution of a polymer, wherein at least 1 wt % of said polymer based on the molecular weight Mw are catechol groups, and wherein the concentration of said polymer in said composition is from 0.1 to 250 mg/ml, b) adjusting the pH of the composition to a value from about 6 to about 7, either (i) before applying the composition to the surface to be coated or (ii) after applying the composition to the surface to be coated, c) applying the composition at least partially to the surface to be coated to obtain an adhesive coating on at least a part of the surface, and d) drying the adhesive coating.

The concentration of the polymer in the solution is calculated in the composition to be applied to the surface, i.e. before the coating is dried.

The adhesive coating can be utilized directly after coating before drying, however it is an advantage that the coating can be dried and subsequently activated by wetting. This feature makes it possible to store the coated object and to handle the coated object in a much easier way. The shelf life is improved compared to a wet coating.

When the dried coating shall be used, an aqueous solution is brought into contact with the adhesive coating to obtain a wetted adhesive coating. The water in the tissue wets and reactivates the dried coating. In one embodiment the coating is reactivated with water from an object that is brought into contact with the coating, for instance biological tissue which is intended to adhere to the coating after reactivation and curing. In one embodiment the coating is brought into contact with a water containing object to obtain a wetted adhesive coating. In one embodiment a coated object is brought into contact with biological tissue, which tissue comprises water. One example is skin or another tissue, which comprises water.

This embodiment has the advantage that the coated object does not have to be wetted in a separate step before use.

In one embodiment a coated implant is brought into contact with tissue which comprises water. The coating is reactivated and will adhere to the tissue. Examples of tissue include but are not limited to skin and bone.

In one embodiment the wetted adhesive coating is brought into contact with at least one other surface and wherein the surfaces are kept in contact for sufficiently long time for curing to occur.

In one embodiment an aqueous solution comprising at least one other substance in addition to water is utilized to reactivate the dried coating. This provides a possibility to add another functional substance to the coating.

In one embodiment the surface to be coated is the surface of a biological tissue.

In one embodiment the surface to be coated is the surface of a metal. In one embodiment the surface to be coated is the surface of a metal alloy. In one embodiment the surface to be coated is the surface of a metal alloy comprising titanium. In one embodiment the surface to be coated is the surface of titanium. In one embodiment the surface to be coated is the surface of a metallic material.

In one embodiment the surface to be coated is the surface of a textile.

In one embodiment the surface to be coated is the surface of a polymeric material. In particular for instance a polymer film is coated. In one embodiment one side of the polymer film is coated. In an alternative embodiment both sides of the polymer film is coated. This latter embodiment gives a double sided adhesive tape. The single sided adhesive film can be utilized for instance as a protection film for wound. The double sided film can be utilized to attach various objects to each other.

Examples of uses of a film coated with the adhesive coating on both sides include but are not limited to attach skin to skin, bone to bone, bone to titanium, and titanium to titanium.

In one embodiment said film comprises at least one selected from the group consisting of polyglycolic acid (PGA), polylactic acid (PLA), poly(lactide-co-glycolide) (PLGA), polydioxanone, caprolactone, hydroxybutyric acid, poly(lactide-co-caprolactone), poly(ethylene oxide) (PEO), chitosan, alginate, hyaluronic acid, modified cellulose, ethylene-vinyl acetate copolymer, polyurethane, collagen, gelatin, and fibrin. Thus also suitable mixtures of polymer may be utilized for a film to be coated.

In one embodiment the osmolarity of the composition is adjusted to a value within ±10% of the osmolarity of the surface of the object to be coated. In one embodiment the osmolarity of the composition is adjusted to a value within ±10% of the osmolarity of the surrounding of surface of the object to be coated. In one embodiment the osmolarity is adjusted to a value below about 300 mOsm/L. In one embodiment the osmolarity is adjusted to a value between 270-330 mOsm/L. It is an advantage in particular for biological applications and medical applications that the osmolarity can be adjusted to a suitable value with regard to the object to be coated. This applies in particular to sensitive objects including biological objects.

As indicated above various types of polymers can be utilized to manufacture the film which is to be coated. Degradable polymers: Polyglycolid, Polyglycolic acid, PGA, Polylactide, Polylactic acid, PLA, Poly(lactide-co-glycolide), PLGA, polydioxanone, caprolactone, Hydroxybutyric acid, Poly(lactide-co-caprolactone), Poly(ethylene oxide), PEO. Polysaccharides: Chitosan, Alginate, Hyaluronic acid, Modified cellulose. Non-degradable polymers: ethylene-vinyl acetate copolymer, polyurethane. Proteins: collagen, gelatin, fibrin.

For biological applications and medical applications it is an advantage that degradable polymer films can be coated. It is further an advantage that the coating is tissue friendly and biocompatible. These features make the coating particularly suitable for biological and medical applications.

In one embodiment the polymer is a protein, which protein comprises 30-3000 amino acids, wherein at least 3% of the amino acid residues of said protein are selected from the group consisting of DOPA (L-3,4-dihydroxyphenylalanine), a DOPA-derivative and combinations thereof.

In one embodiment 6-30 wt % of the polymer based on the molecular weight Mw are at least one moiety selected from DOPA (L-3,4-dihydroxyphenylalanine), a DOPA-derivative and combinations thereof.

In one embodiment the at least one polymer is a protein which is extracted from a byssus-forming mussel.

In one embodiment the at least one protein is a protein manufactured by recombinant DNA technology. In one embodiment the at least one protein is a synthetic protein.

In one embodiment the at least one polymer is a protein comprising tandemly linked peptide repeats comprising 3-15 amino acid residues each.

In one embodiment the at least one polymer is mussel adhesive protein. In one embodiment the protein is at least one polymer is at least one protein selected from the group consisting of MEFP-1, MEFP-2, MEFP-3, MEFP-4, and MEFP-5. (*Mytilus edulis* foot protein, 1, 2, 3, 4, and 5 respectively.). In one embodiment protein is at least one protein selected from the group consisting of foot protein 1-5 (FP1, FP2, FP3, FP4, and FP5) derived from a *Mytilus specie*. In one embodiment the concentration of MEFP is between 10 and 250 mg/ml in the composition before it has dried.

In one embodiment the concentration of the polymer is between 10 and 250 mg/ml in the composition before it has dried. In an alternative embodiment the concentration of the polymer is between 1 and 250 mg/ml in the composition before it has dried.

In one embodiment the composition further comprises at least one filler. In one embodiment the filler comprises biodegradable polymer particles with an average diameter in the range from 10 nm to 500 µm. In one embodiment the filler comprises inorganic particles with an average diameter in the range from 10 nm to 500 µm. In one embodiment the composition further comprises filler particles comprising at least one compound selected from cellulose and hyaluronic acid. In one embodiment the composition further comprises filler particles comprising at least one compound selected from microcrystalline cellulose and modified cellulose. In one embodiment the composition further comprises filler particles comprising at least one compound selected from microcrystalline cellulose and modified cellulose with an average diameter in the range from 25 µm to 200 µm. In one embodiment the filler particles have a diameter in the range from 25 µm to 200 µm. In one embodiment the filler particles have an average size from 10 nm to 500 µm. In an alternative embodiment the filler particles have an average size from 10 nm to 1 µm.

In one embodiment said composition further comprises at least one drug compound. In one embodiment said drug is a growth factor. In an embodiment where the adhesive further comprises a drug it is possible to use the coating as a carrier for a drug molecule. In one embodiment the adhesive is used in an application in contact with bone and the coating comprises a growth factor.

In one embodiment said composition further comprises at least one antimicrobial compound.

In one embodiment said composition further comprises at least one particle.

In one embodiment the composition comprises at least one compound which is basic in aqueous solution. In one embodiment the compound is selected from $Na_2CO_3$, $Na_3PO_4$, and NaOH.

In one embodiment the composition is applied at a temperature in the interval 5-95° C.

In one embodiment the object onto which the adhesive coating is applied comprises at least one material selected from glass, titanium, and polyurethane.

In other embodiments the adhesive coating is applied on a material comprising a polymer.

In another aspect there is provided an object comprising a dried coating, wherein said coating comprises at least one polymer, wherein at least 1 wt % of the polymer based on the molecular weight Mw are catechol groups.

The embodiments of the object are the same as for the method described above. Thus the object can be a film, the coating may comprise for instance a filler and a drug compound.

There is further provided a kit for applying an adhesive coating to the surface of an object, said kit comprising: a) a composition comprising a solution of a polymer, wherein at least 1 wt % of the polymer based on the molecular weight Mw are chatechol groups, and wherein the concentration of said polymer in said composition is from 0.1 to 250 mg/ml, b) an instruction to adjust the pH of the composition to a value from about 6 to about 7, either (i) before applying the composition to the surface to be coated or (ii) after applying the composition to the surface to be coated and an instruction to apply the composition at least partially to the surface to be coated to obtain an adhesive coating on at least a part of the surface, and c) an instruction to dry the adhesive coating.

In one embodiment the kit comprises a basic solution. In an alternative solution the kit comprises a compound which in aqueous solution is basic.

In one embodiment the kit further comprises an instruction to wet the dried adhesive coating with water. In one embodiment the kit comprises an instruction to wet the dried adhesive with a tissue comprising water. In one embodiment the kit comprises an instruction to bring the dried adhesive into contact with a tissue. In another embodiment the kit comprises an instruction to bring the wetted adhesive coating into contact with at least one other surface and to keep the surfaces in contact for sufficiently long time for curing to occur. In yet another embodiment the kit comprises an instruction to coat a biological tissue. In one embodiment the kit further comprising an instruction to bring the composition in contact with a biological tissue.

Other features and uses of the invention and their associated advantages will be evident to a person skilled in the art upon reading the description and the examples.

It is to be understood that this invention is not limited to the particular embodiments shown here. The following examples are provided for illustrative purposes and are not intended to limit the scope of the invention since the scope of the present invention is limited only by the appended claims and equivalents thereof.

EXAMPLES

Example 1

Optimal curing conditions for MEFP-1 at two different protein concentrations, using sodium carbonate to adjust pH.

MEFP-1 solutions of two different concentrations were tested and compared. The concentrations were 60 mg/ml and 110 mg/ml and sodium carbonate solutions were used for adjusting pH. In order to determine the optimal curing conditions, the adhesive strength between two glass plates was determined. The MEFP-1 solution was applied to one of the glass plates followed by a sodium carbonate solution in a 1:1 ratio. The two components were mixed and spread using a plastic toothpick. The glass plates were assembled with 2 cm overlap. The plates were clamped and the adhesive was allowed to cure for 3 h at 30° C. The shear strength was determined at a cross head speed of 10 mm/min. In each set of measurements 14 pairs of glass plates were glued. All calculations are made based on the 10 values in the middle. The pH of the compositions was measured using a pH-meter after mixing MEFP-1 solution and sodium carbonate solution in a 1:1 ratio resulting in a final volume of 150 µl. The pH was checked directly after mixing and after 3 h. The optimal strength for both protein concentrations is reached when pH after mixing with sodium carbonate is between 6 and 7 (see table 1).

TABLE 1

Measurements of pH and adhesive strength for different bioadhesive compositions of MEFP-1 and sodium carbonate. The optimal conditions for each protein concentration are highlighted in bold.

| MEFP-1 conc. (mg/ml) | $Na_2CO_3$ conc. (M) | pH after 3 h | Bond Strength (kPa) |
|---|---|---|---|
| 60 | 0 | 3 | 51.5 ± 4.9 |
| 60 | 0.05 | 4.6 | 58.5 ± 10.2 |
| 60 | 0.08 | 5.6 | 135.7 ± 32.7 |
| 60 | 0.10 | 6.2 | 218.0 ± 19.5 |
| 60 | 0.12 | 6.8 | 219.1 ± 28.8 |
| 60 | 0.14 | 7.3 | 163.6 ± 19.8 |
| 60 | 0.2 | 8.0 | 115.6 ± 11.5 |
| 60 | 0.3 | 9.3 | 72.1 ± 13.7 |
| 110 | 0 | 3.2 | 59.4 ± 13.5 |
| 110 | 0.1 | 5.6 | 83.8 ± 27.9 |
| 110 | 0.12 | 6 | 260.7 ± 16.9 |
| 110 | 0.14 | 6.5 | 262.8 ± 48.7 |
| 110 | 0.16 | 6.8 | 193.4 ± 29.2 |
| 110 | 0.2 | 7.4 | 116.0 ± 15.9 |
| 110 | 0.27 | 8.5 | 106.8 ± 15.0 |

Example 2

Optimal curing conditions for MEFP-1, 60 mg/ml using sodium carbonate, sodium phosphate or sodium hydroxide to adjust pH.

A MEFP-1 solution with a concentration of 60 mg/ml was mixed with a basic solution in order to adjust pH. Three different bases were compared, sodium carbonate, sodium phosphate and sodium hydroxide. In order to determine the optimal curing conditions, the adhesive strength between two glass plates was determined. The MEFP-1 solution was applied to one of the glass plates followed by the basic solution in a 1:1 ratio. The two components were mixed and spread using a plastic toothpick. The glass plates were assembled with 2 cm overlap. The plates were clamped and the adhesive was allowed to cure for 3 h at 30° C. The shear strength was determined at a cross head speed of 10 mm/min.

In each set of measurements 14 pairs of glass plates were glued. All calculations are made based on the 10 values in the middle. The pH of the compositions was measured using a pH-meter after mixing MEFP-1 solution and the basic solution in a 1:1 ratio resulting in a final volume of 150 µl. The pH was checked directly after mixing and after 3 h. The optimal strength for all compositions is reached when pH after mixing is between 6 and 7 (see table 2).

TABLE 2

Measurements of pH and adhesive Strength for different Bioadhesive compositions of MEFP-1 using three different bases for adjusting pH. The optimal conditions are highlighted in bold for each base.

| MEFP-1 conc. (mg/ml) | Base | Base conc. (M) | pH after 3 h | Bond Strength (kPa) |
| --- | --- | --- | --- | --- |
| 60 | $Na_2CO_3$ | 0 | 3 | 51.5 ± 4.9 |
| 60 | $Na_2CO_3$ | 0.05 | 4.6 | 58.5 ± 10.2 |
| 60 | $Na_2CO_3$ | 0.08 | 5.6 | 135.7 ± 32.7 |
| 60 | $Na_2CO_3$ | 0.10 | 6.2 | 218.0 ± 19.5 |
| 60 | $Na_2CO_3$ | 0.12 | 6.8 | 219.1 ± 28.8 |
| 60 | $Na_2CO_3$ | 0.14 | 7.3 | 163.6 ± 19.8 |
| 60 | $Na_2CO_3$ | 0.2 | 8.0 | 115.6 ± 11.5 |
| 60 | $Na_2CO_3$ | 0.3 | 9.3 | 72.1 ± 13.7 |
| 60 | $Na_3PO_4$ | 0.06 | 5.1 | 88.6 ± 16.4 |
| 60 | $Na_3PO_4$ | 0.08 | 5.7 | 112.6 ± 13.0 |
| 60 | $Na_3PO_4$ | 0.09 | 5.9 | 116.4 ± 26.4 |
| 60 | $Na_3PO_4$ | 0.11 | 6.5 | 265.2 ± 24.2 |
| 60 | $Na_3PO_4$ | 0.14 | 7 | 135.9 ± 15.1 |
| 60 | $Na_3PO_4$ | 0.17 | 8.1 | 114.6 ± 23.7 |
| 60 | NaOH | 0.12 | 5.5 | 90.5 |
| 60 | NaOH | 0.13 | 5.7 | 117.3 |
| 60 | NaOH | 0.14 | 6 | 186.0 |
| 60 | NaOH | 0.15 | 6.2 | 185.8 |
| 60 | NaOH | 0.16 | 6.8 | 178.1 |
| 60 | NaOH | 0.18 | 9.3 | 124.8 |

Example 3

Drying the bioadhesive followed by reactivation with water.

A MEFP-1 solution with a concentration of 60 mg/ml was mixed with a sodium phosphate solution in order to adjust pH to optimal curing conditions, i.e. pH 6.5. The MEFP-1 solution was applied to one of the glass plates followed by the Na3PO4 solution (0.11 M) in a 1:1 ratio. The two components were mixed and spread using a plastic toothpick. The bioadhesive composition covered a surface of 2×2.5 cm. After application the bioadhesive was allowed to dry for 72 h at RT. After drying the plates were dipped in water and assembled with a clean glass plate with 2 cm overlap. The plates were clamped and the adhesive was allowed to cure for 3 h at 30° C. The shear strength was determined at a cross head speed of 10 mm/min. In each set of measurements 14 pairs of glass plates were glued. All calculations are made based on the 10 values in the middle. The strength of the dried and reactivated bioadhesive is comparable with the strength of the bioadhesive that was applied and cured directly (see table 3).

TABLE 3

Measurements of adhesive strength for one of the optimal bioadhesive compositions. In one set of measurements the glass plates were assembled and the bioadhesive was cured right after application. In the other set of measurements the bioadhesive was dried for 72 h followed by reactivation with water. After reactivation the plates were assembled and the bioadhesive was cured.

| Bioadhesive condition | MEFP-1 conc. (mg/ml) | $Na_3PO_4$ conc. (M) | pH after 3 h | Bond Strength (kPa) |
| --- | --- | --- | --- | --- |
| Applied right before use | 60 | 0.11 | 6.5 | 265.2 ± 24.2 |
| Dried and reactivated | 60 | 0.11 | 6.5 | 225.5 ± 45.1 |

Example 4

Drying the bioadhesive film at different temperatures followed by activation with water—glass surface.

A MEFP-1 solution with a concentration of 60 mg/ml in 1% citric acid was mixed with a sodium phosphate solution in order to adjust pH to optimal curing conditions, i.e. pH 6.5. The MEFP-1 solution was applied to glass plates followed by the $Na_3PO_4$ solution (0.11 M) in a 1:1 ratio. The two components were mixed and spread using a plastic toothpick. The bioadhesive composition covered a surface of 2×2.5 cm and the surface concentration was approximately 120 µg protein/cm². After application, one set of plates were allowed to dry at 30° C. for 30 minutes and a second set of plates were allowed to dry at 80° C. for 30 minutes. After drying the dry bioadhesive film was activated by wetting with water and assembled with clean glass plates with 2 cm overlap. The plates were clamped and the activated adhesive was allowed to cure for 3 h at 30° C. The shear strength was determined at a cross head speed of 10 mm/min. In each set of measurements 14 or 15 pairs of glass plates were glued. All calculations are made based on the 10 or 11 values in the middle. The results are presented in FIG. 2 and compared with the results for films dried in RT (example 3). The strength of the reactivated dry bioadhesive films are comparable for films dried at RT for 72 h, at 30° C. for 30 minutes and at 80° C. for 30 minutes.

Figure 1:
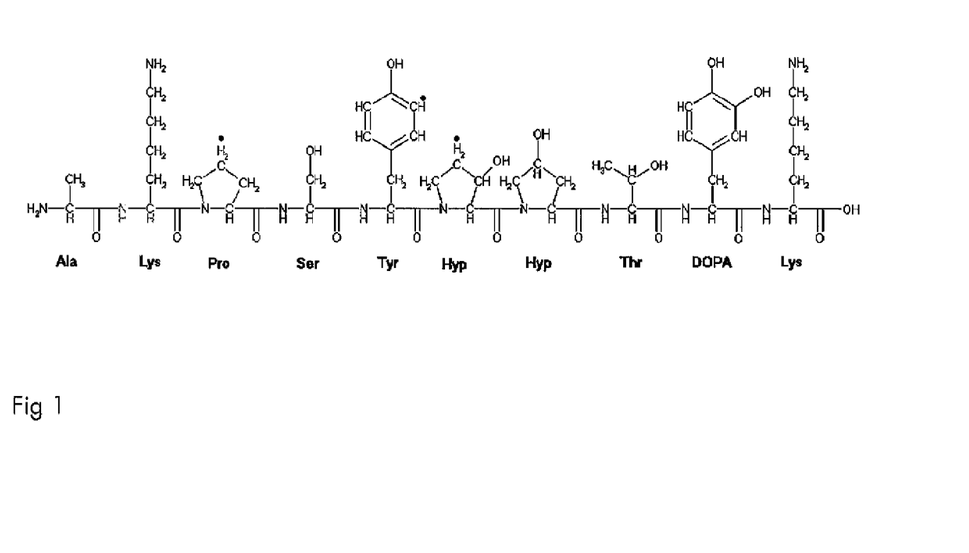
FIG. 1 shows a common repeating unit in MEFP-1 with 10 amino acids. (Ala, Lys, Pro, Ser, Tyr, Hyp, Hyp, Thr, DOPA, Lys)
Figure 2:
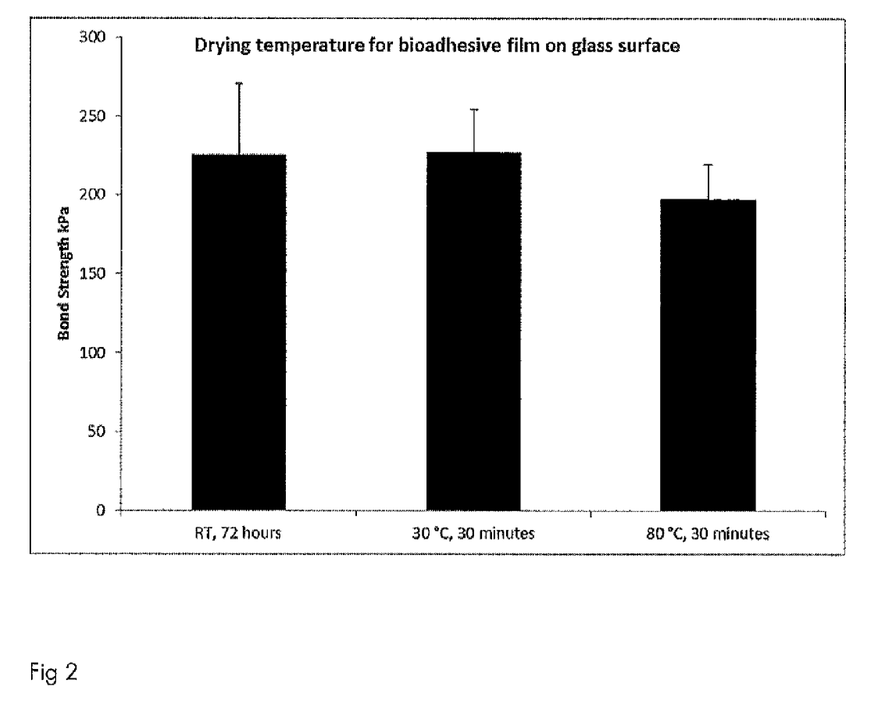
FIG. 2 shows the effect of the drying temperature, FIG. 3 also shows the effect of the drying temperature.

The bioadhesive composition was applied to one of the surfaces and thereafter dried at different conditions, i.e. at RT, 30° C. and 80° C. The dried films were activated by addition of water and assembled with a second surface. The resulting bond strength is shown in FIG. 2 for films dried at RT, 30° C. and 80° C. The different drying conditions result in similar bond strength.

Example 5

Drying the bioadhesive film at different temperatures followed by activation with water—titanium surface.

A MEFP-1 solution with a concentration of 60 mg/ml in 1% citric acid was mixed with a sodium phosphate solution in order to adjust pH to optimal curing conditions, i.e. pH 6.5. The MEFP-1 solution was applied to titanium plates followed by the $Na_3PO_4$ solution (0.11 M) in a 1:1 ratio. The two components were mixed and spread using a plastic toothpick. The bioadhesive composition covered a surface of 2×1.35 cm and the surface concentration was approximately 220 µg protein/cm². After application, one set of plates were allowed to dry at RT° C. for approximately 3 h and a second set of plates were allowed to dry at 80° C. for 30 minutes. After drying the bioadhesive films were activated by wetting with water and assembled with clean titanium plates with 2 cm overlap. The plates were clamped and the activated adhesive was allowed to cure for 3 h at 30° C. The shear strength was determined at a cross head speed of 10 mm/min. In each set of measurements 5 pairs of titanium plates were glued. All calculations are made based on the 3 values in the middle. The results are presented in FIG. 3. The strength of the reactivated dry bioadhesive films on titanium plates, are comparable for films dried at RT and films dried at 80° C.

Figure 3:
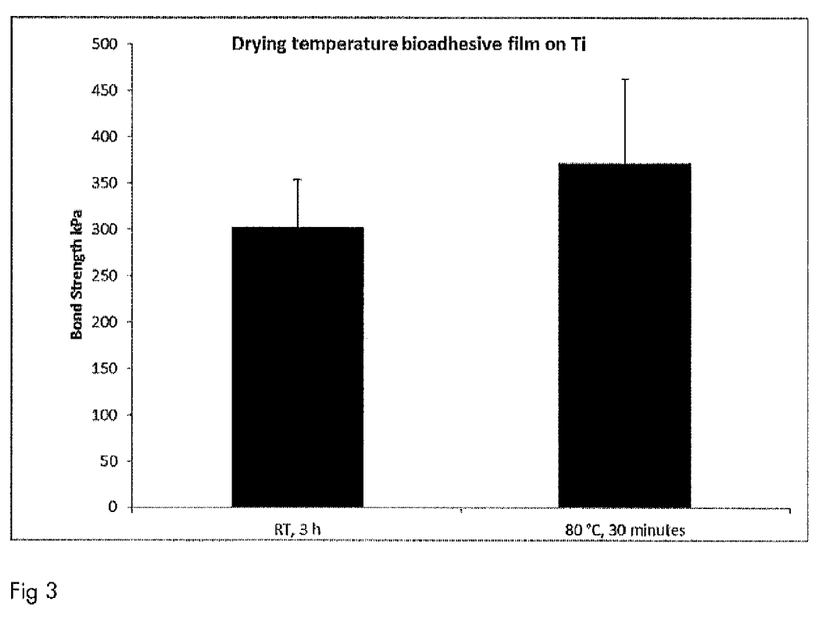

The bioadhesive composition was applied to one of the titanium surfaces and thereafter dried at different conditions, i.e. at RT or 80° C. The dried films were activated by addition of water and assembled with a second titanium surface. The resulting bond strength is shown in FIG. 3 for films dried at RT and 80° C. The different drying conditions result in similar Bond strength.

Example 6

Figure 4:
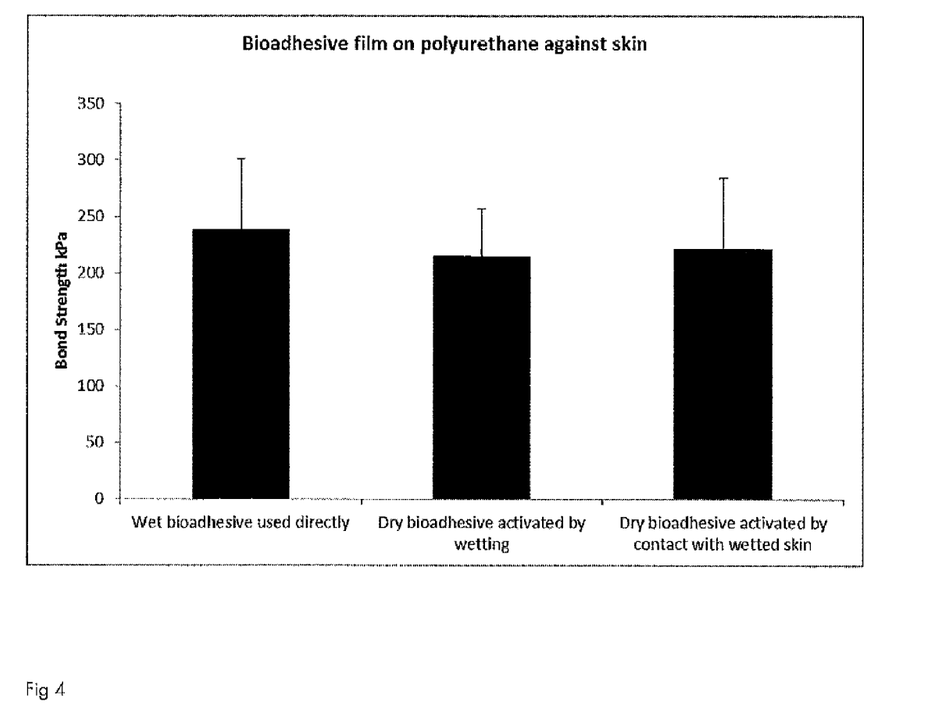
FIG. 4 shows a comparison between dried adhesive and non-dried adhesive.

Using the dry bioadhesive film for attaching skin to polyurethane—Different strategies for activation A MEFP-1 solution with a concentration of 60 mg/ml in 1% citric acid was mixed with a sodium phosphate solution in order to adjust pH to optimal curing conditions, i.e. pH 6.5. The MEFP-1 solution was applied to one side of a polyurethane cube (12×12×12 mm) followed by the $Na_3PO_4$ solution (0.11 M) in a 1:1 ratio. The two components were mixed and spread using a plastic toothpick. The surface concentration of the bioadhesive was approximately 420 µg protein/cm². For one set of cubes, the bioadhesive composition was used directly, without drying, by attaching another cube covered with a porcine split thickness skin graft. The two remaining sets of cubes, covered with the bioadhesive composition, were allowed to dry at 30° C. for 30 minutes. The first set of cubes with dry bioadhesive film was activated by wetting the bioadhesive film followed by assembling with another cube covered by a porcine split thickness skin graft. The second set of cubes with dry bioadhesive film was activated by wetting the porcine split thickness skin graft before assembling with the dry bioadhesive film. The pairs of cubes were clamped and allowed to cure for 3 h at 30° C. The tensile strength was determined at a cross head speed of 10 mm/min. In each set of measurements 5 were glued. All calculations are made based on 5 values. The results are presented in FIG. 4. The strength of the activated dry bioadhesive films on polyurethane surfaces with different wetting strategies are compared with the bioadhesive composition when used directly. The resulting bond strengths are similar for all sets of measurements.

The bioadhesive composition was applied to polyurethane cubes. One set of cubes were used directly by assembling with another set of cubes covered with porcine split thickness skin graft. For two sets of cubes, the bioadhesive was dried and later activated by wetting with water and or by contact with wetted skin. Both sets were assembled with cubes covered with porcine split thickness skin graft. After curing at 30° C. for 3 h, all sets of experiments show similar tensile strength according to FIG. 4

Example 7

Using the dry bioadhesive film for attaching bone to titanium—Different strategies for film formation MEFP-1 solutions in 1% citric acid was mixed with a sodium phosphate solution in order to adjust pH to optimal curing conditions, i.e. pH 6.5. Dried bioadhesive films were formed in different ways described in A)-F) (below). In all sets of experiments the bioadhesive film covered a surface of 2×1.35 cm and were dried at 37° C. for 30 minutes. A): MEFP-1, 60 mg/ml in 1% citric was applied to titanium plates followed by the $Na_3PO_4$ solution (0.11 M) in a 1:1 ratio. The two components were mixed and spread using a plastic toothpick. The surface concentration was approximately 220 µg protein/cm². B): MEFP-1, 60 mg/ml in 1% citric was premixed with $Na_3PO_4$ solution (0.11 M) in a 1:1 ratio. The mixed bioadhesive was applied to titanium surfaces and spread using a plastic toothpick. The surface concentration was approximately 220 µg protein/cm². C): MEFP-1, 60 mg/ml in 1% citric was applied to titanium plates and spread using a plastic toothpick. The protein layers were dried at 37° C. followed by applying the $Na_3PO_4$ solution (0.11 M) in a 1:1 ratio (MEFP1:$Na_3PO_4$). The films were dried at RT. The surface concentration was approximately 220 µg protein/cm². D): Film formation was done as for B) but double volume was applied, i.e. premixing the two components and applying at a surface concentration of approximately 440 µg protein/cm². E): Film formation was done as for B) but MEFP-1, 100 mg/ml was premixed with $Na_3PO_4$ solution (0.11 M) in a ratio of 1:1. The surface concentration was approximately 370 µg protein/cm². F): Film formation was done as for C) but MEFP-1, 100 mg/ml in 1% citric was used instead of 60 mg/ml. The surface concentration was approximately 370 µg protein/cm².

Figure 5:
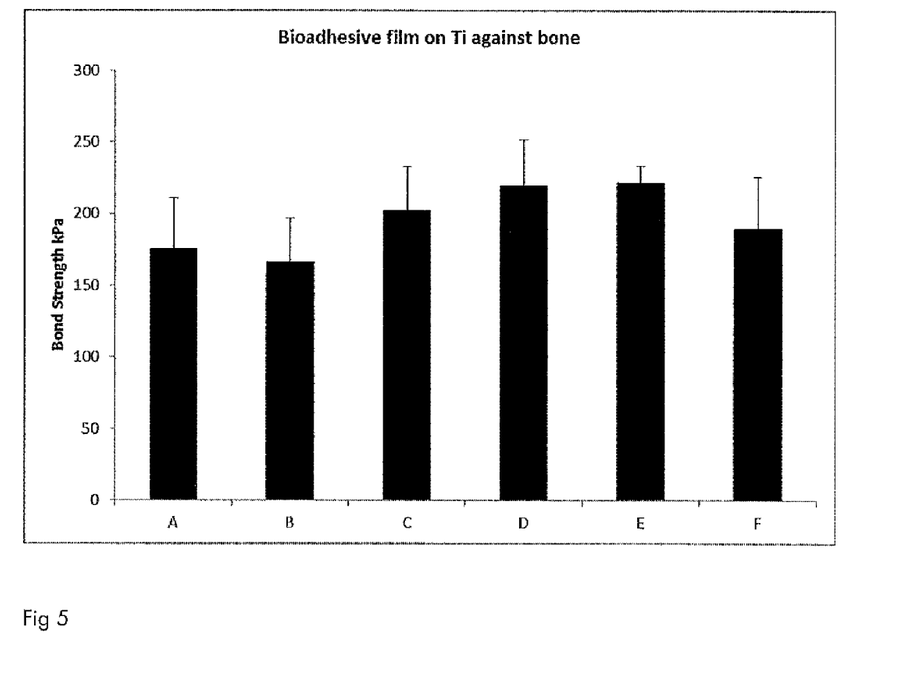
FIG. 5 shows the bond strength for different coated films.

After drying the bioadhesive films were activated by contact with a wetted piece of bone. The bone and titanium plate were assembled and clamped and allowed to cure for 1 h at 37° C. The tensile strength was determined at a cross head speed of 10 mm/min. In each set of measurements 5 pairs of bone/titanium were glued. All calculations are made based on the 3 values in the middle. The results are presented in FIG. 5. The bond strength for bone to the activated dry bioadhesive films on titanium plates is similar for different film formation strategies but increases slightly at higher surface concentration.

The bioadhesive film was applied to titanium surfaces using different strategies for film formation and different final surface concentration. The dried films were activated by contact with a wetted piece of bone. After curing for 1 h at 37° C. it was shown that different film formation strategies result in similar tensile strength between titanium and bone whereas a higher surface concentration slightly increases the tensile strength, see FIG. 5.

Example 8

Apply the dry adhesive film on both sides of a thin polymeric film and using the resulting double adhesive tape to attach skin to skin.

Thin films of bioresorbable polymer, Poly(D,L-lactide) (PLA) or Poly(D,L-lactide-co-glycolide) (PLGA 50:50) was formed by solvent casting. The polymer solution was spread on a glass plate, by hand or using a bird film applicator, followed by drying. The film could be removed from the glass plate after immersion in water. The thicknesses of the films were approximately 20-50 µm. MEFP-1, 60 mg/ml in 1% citric was applied to one side of the polymer film. The protein solution was spread with a plastic toothpick. An equal volume of $Na_3PO_4$ solution (0.11 M) was spread on top of the MEFP-1 layer. The bioadhesive film was allowed to dry and the procedure was repeated on the second side of the polymer film. On the PLA film the surface concentration of the bioadhesive film was approximately 230 µg protein/cm²/side and for the PLGA film the surface concentration was approximately 450 µg protein/cm²/side. The films were divided into smaller pieces before use.

Figure 6:
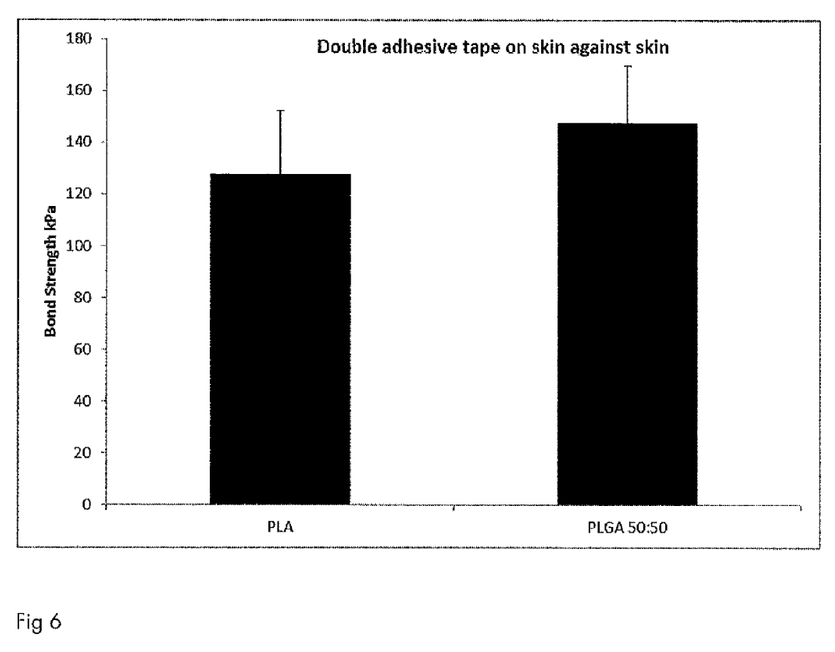
FIG. 6 shows the bond strength for films of PLA and PLGA.

Polyurethane cubes covered by porcine split thickness skin graft were wetted by water. The dry bioadhesive film on the double adhesive tape was activated by contact with the wet skin. Each piece of tape was used to attach two cubes covered with skin. The cubes were clamped and the tape was allowed to cure for 3 h at 30° C. The tensile strength was determined at a cross head speed of 10 mm/min. In each set of measurements 14 pairs of skin covered cubes were glued. All calculations are made based on the 10 values in the middle. The results for the double adhesive tape formed on a thin film of PLA or a thin film of PLGA are presented in FIG. 6. The bond strength for attachment of skin to skin is similar for the dry bioadhesive film applied to the two different polymers.

The bioadhesive composition was applied to both sides of a bioresorbable thin polymer film. The resulting double adhesive tape was used to attach two polyurethane cubes covered with porcine split thickness skin graft. The dry bioadhesive film was activated by contact with wet skin. After curing at 30° C. for 3 h, the double adhesive tapes made of two different bioresorbable polymers show similar tensile strength, according to FIG. 6.

Example 9

Apply the dry adhesive film on both sides of a thin polymeric film and using the resulting double adhesive tape to attach bone to titanium.

Thin films of bioresorbable polymer, PLGA 75:25 and PLGA 50:50 were formed by solvent casting. The polymer solution was spread on a glass plate using a bird film applicator, followed by drying. Films of Polyglycolide (PGA) were formed by melting the polymer at 350° C. between two glass plates. After melting a slight pressure was applied to the plates resulting in formation of a thin film. All films were removed from the glass plates after immersion in water. The thicknesses of the films were approximately 70-90 µm. MEFP-1, 60 mg/ml in 1% citric was applied to one side of the polymer film. The protein solution was spread with a plastic toothpick. An equal volume of $Na_3PO_4$ solution (0.11 M) was spread on top of the MEFP-1 layer. The bioadhesive film was allowed to dry and the procedure was repeated on the second side of the polymer film. The surface concentration of the bioadhesive film was approximately 460 µg protein/cm²/side for PLGA 75:25, 450 µg protein/cm²/side for PLGA 50:50 and 400 µg protein/cm²/side for PGA. The films were divided into smaller pieces before use.

Figure 7:
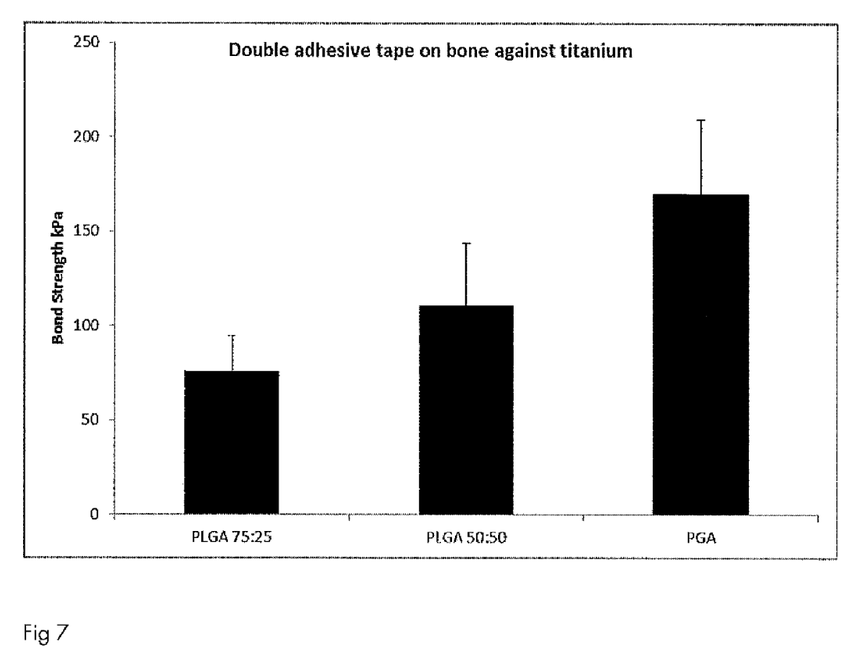
FIG. 7 shows the bond strength for films of PGA and PLGA in different compositions.

The pieces of double adhesive tape were activated by contact with a wetted piece of bone on one side and a wetted titanium plate on the other side. The assembly was clamped and allowed to cure for 1 h at 37° C. The tensile strength was determined at a cross head speed of 10 mm/min. In each set of measurements 3-6 pairs of bone/double adhesive tape/titanium were glued. The results are presented in FIG. 7. The double adhesive tapes result in efficient bonding of bone to titanium regardless of underlying polymer. The bond strength is increasing with increasing glycolide:lactide ratio and reaches the highest value for pure PGA.

The bioadhesive composition was applied to both sides of a bioresorbable thin polymer film. The resulting double adhesive tape was used to attach pieces of bone to titanium plates. The dry bioadhesive film was activated by contact with wet bone on one side and the wetted titanium plate on the other side. After curing at 37° C. for 1 h, the tensile strength was measured. The double adhesive tapes result in efficient bonding of bone to titanium regardless of polymer but the strength is increasing with increasing glycolide:lactide ratio, see FIG. 7.

Evaluation of Double Sided Adhesive Tape for Storage and γ-Sterilization

Thin films of bioresorbable polymer PLGA 50:50 were formed by solvent casting. The polymer solution was spread on a glass plate using a bird film applicator, followed by drying. The films were removed from the glass plates after immersion in water. The thicknesses of the films were approximately 70-90 µm. MEFP-1, 60 mg/ml in 1% citric was applied to one side of the polymer film. The protein solution was spread with a plastic toothpick. An equal volume of $Na_3PO_4$ solution (0.11 M) was spread on top of the MEFP-1 layer. The bioadhesive film was allowed to dry and the procedure was repeated on the second side of the polymer film. The surface concentration of the bioadhesive film was approximately 450 µg protein/cm²/side. The films were divided into smaller pieces of double sided adhesive tape.

Figure 8:
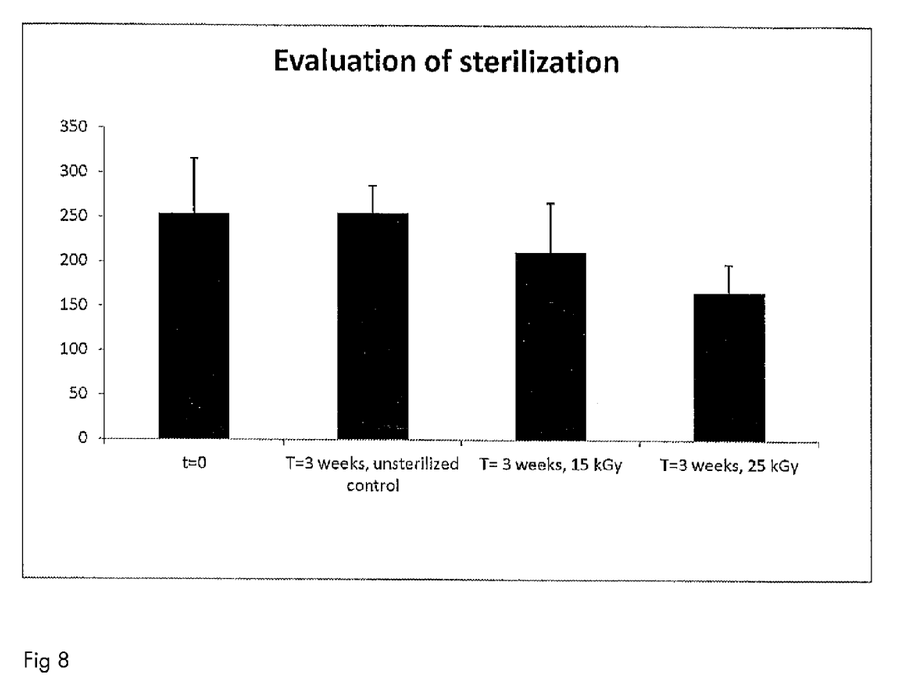
FIG. 8 shows the bond strength for films of PLGA after storage and sterilization.

The pieces of double sided adhesive tape was packed in Al-pouches in N2-atmosphere. 4 sets of 14 pieces of tape were packed. One set was tested directly (T=0), one set was kept as unsterilized control, one was sterilized at 15 kGy and one at 25 kGy. All pieces of tape were tested for bond strength when used for attaching titanium to titanium. The dimension of the bonded area was 1.35×2 cm and the bioadhesive film was activated by wetting the double sided adhesive tape with water. After attachment the titanium plates were clamped and the adhesive tape was allowed to cure for 3 h at 37° C. The shear strength was determined at a cross head speed of 10 mm/min. In each set of measurements 14 pairs of titanium plates were glued. All calculations are made based on the 10 values in the middle. The unsterilized control is unchanged compare to the control at T=0. For the γ-sterilized samples there was a decrease in bond strength. The bond strength was decreased to 83.2% of the control for samples sterilized at 15 kGy and 65.1% of the control, for samples treated at 25 kGy (FIG. 8).

The invention claimed is:
1. A method for applying an adhesive coating to the surface of an object, said method comprising the steps of:
  a) providing a composition comprising a solution of a polymer, wherein at least 1 wt % of said polymer based on the molecular weight Mw are catechol groups, and wherein the concentration of said polymer in said composition is from 0.1 to 250 mg/ml,
  b) adjusting the pH of the composition to a value from about 6 to about 7, either (i) before applying the composition to the surface to be coated or (ii) after applying the composition to the surface to be coated,
  c) applying the composition at least partially to the surface to be coated to obtain an adhesive coating on at least a part of the surface,
  d) drying the adhesive coating;
  e) i) bringing an aqueous solution into contact with the dried adhesive coating to obtain a wetted adhesive coating or ii) bringing the coating into contact with a water-containing object to obtain a wetted adhesive coating;
  f) bringing the wetted adhesive coating into contact with at least one other surface and wherein the surfaces are kept in contact for sufficiently long time for curing to occur; and wherein the surface to be coated is the surface of a biological tissue.
2. The method according to claim 1, wherein the polymer is a protein, which protein comprises 30-3000 amino acids, wherein at least 3% of the amino acid residues of said protein are selected from the group consisting of DOPA (L-3,4-dihydroxyphenylalanine), a DOPA-derivative and combinations thereof.

3. The method according to claim 1, wherein 6-30 wt % of the polymer based on the molecular weight Mw are at least one moiety selected from DOPA (L-3,4-dihydroxyphenylalanine), a DOPA-derivative and combinations thereof.

4. The method according to claim 1, wherein the at least one polymer is a protein which is extracted from a byssus-forming mussel.

5. The method according to claim 1, wherein the at least one polymer is a protein comprising tandemly linked peptide repeats comprising 3-15 amino acid residues each.

6. The method according to claim 1, wherein the at least one polymer is mussel adhesive protein.

7. The method according to claim 1, wherein the polymer is at least one protein selected from the group consisting of foot protein 1, foot protein 2, foot protein 3, foot protein 4, foot protein 5, derived from a Mytilus specie.

8. The method according to claim 1, wherein the composition further comprises at least one filler.

9. The method according to claim 8, wherein said filler comprises inorganic particles with an average diameter in the range from 10 nm to 500 µm.

10. The method according to claim 8, wherein said filler comprises biodegradable polymer particles with an average diameter in the range from 10 nm to 500 µm.

11. The method according to claim 10, wherein said filler comprises at least one compound selected from the group consisting of microcrystalline cellulose and modified cellulose.

12. The method according to claim 1, wherein said composition further comprises at least one drug compound.

13. The method according to claim 12, wherein said drug is a growth factor.

14. The method according to claim 1, wherein said composition further comprises at least one antimicrobial substance.

* * * * *